Figure 1:
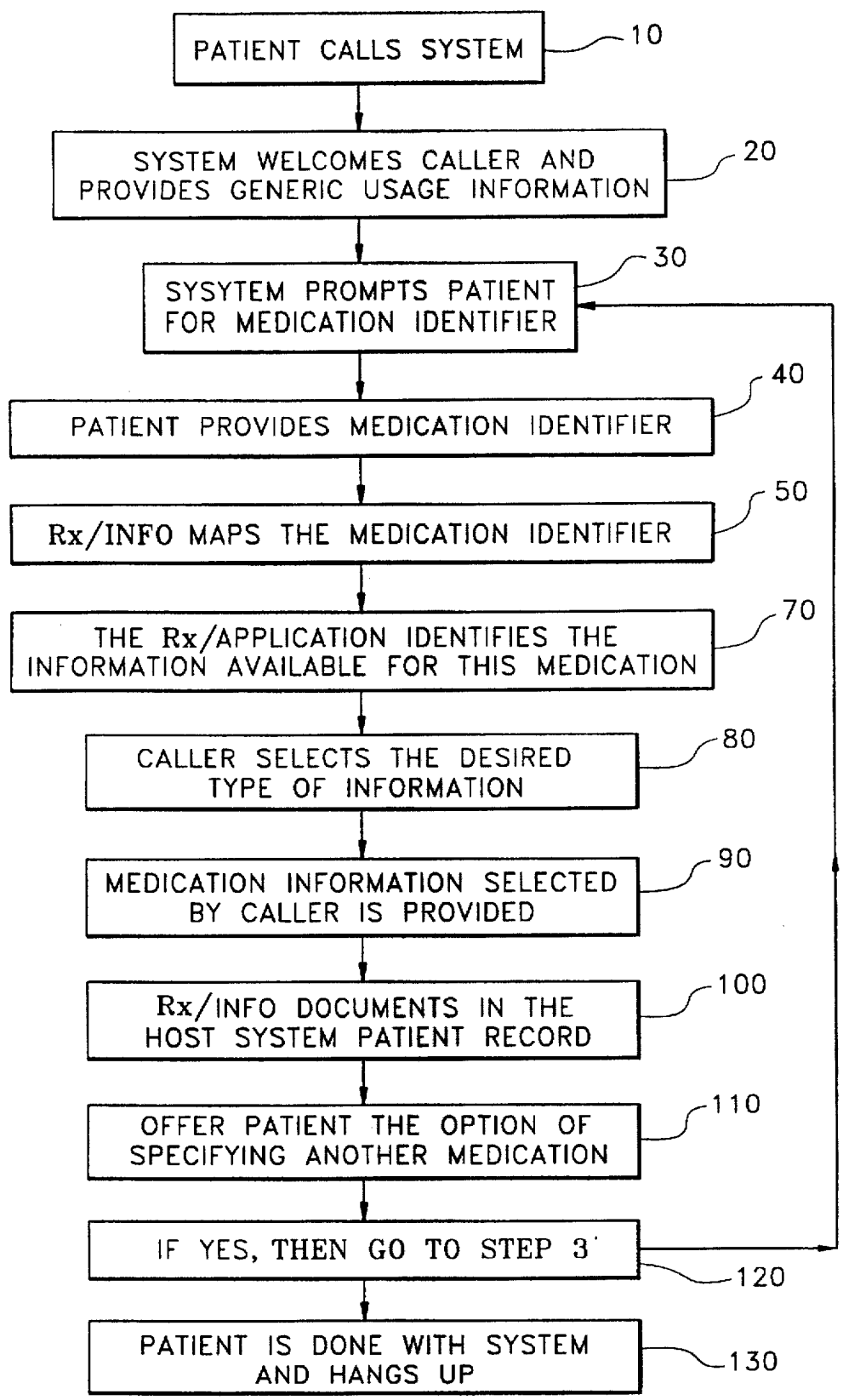

United States Patent [19]

Garcia

[11] Patent Number: 5,737,396
[45] Date of Patent: Apr. 7, 1998

[54] INTERACTIVE MEDICATION DATA TELEPHONY SYSTEM

[75] Inventor: Alfredo Garcia, Coral Gables, Fla.

[73] Assignee: Mumps AudioFAX, Inc., Wayne, Pa.

[21] Appl. No.: 786,088

[22] Filed: Jan. 17, 1997

Related U.S. Application Data

[63] Continuation of Ser. No. 515,250, Aug. 15, 1995, abandoned.

[51] Int. Cl.$^6$ .................................................. H04M 1/64
[52] U.S. Cl. ........................... 379/88; 379/67; 379/201; 364/400
[58] Field of Search ........................... 379/67, 88, 89, 379/97, 201, 207, 350, 73, 74, 77, 87, 90; 364/400, 284, 282.1, 413.01, 413.02, 413.06, 413.04; 395/2.79, 2.84; 221/2, 3

[56] References Cited

U.S. PATENT DOCUMENTS

| | | | |
|---|---|---|---|
| 4,539,435 | 9/1985 | Eckmann . | |
| 4,766,542 | 8/1988 | Pilarczyk . | |
| 4,847,764 | 7/1989 | Halvorson . | |
| 4,899,839 | 2/1990 | Dessertine . | |
| 5,016,172 | 5/1991 | Dessertine . | |
| 5,164,981 | 11/1992 | Mitchell et al. | 379/88 |
| 5,199,062 | 3/1993 | Von Meister et al. | 379/207 |
| 5,225,976 | 7/1993 | Tawil . | |
| 5,299,121 | 3/1994 | Brill et al. | 364/413.01 |
| 5,329,459 | 7/1994 | Kaufman et al. | 364/413.02 |
| 5,337,347 | 8/1994 | Halstead-Nussloch et al. | 379/88 |
| 5,345,501 | 9/1994 | Shelton | 379/88 |
| 5,390,238 | 2/1995 | Kirk et al. | 379/93 |
| 5,404,295 | 4/1995 | Katz et al. | 364/419.19 |
| 5,454,063 | 9/1995 | Rossides | 395/2.84 |
| 5,509,064 | 4/1996 | Welner et al. | 379/265 |
| 5,612,869 | 3/1997 | Letzt et al. | 395/203 |

OTHER PUBLICATIONS

MUMPS AudioFAX Trade Literature entitled "DHCP–Rx/INFO", Jul. 6, 1994 (limited distribution).
Veterans' Administration invoice for "Order No. 402–A37635", Aug. 16, 1994.
"Walgreens continuew to set the standard for drugs chains, Plans to increase its Market Share & Boost Customer Convenience", Chain Drug Review, p. 75, May 1, 1995.
"Walgreens Readies Assult on 2 Markets", Drug Store News, p. 4, James Frederick, Feb. 6, 1995.
"High–Tech Rx for Walgreen Pharmacies, Will roll out a high–tech Pharmacy system in Apr. 1995 that it expects to revolutionize the industry", chicago Sun Time (IL), p. 49, Jan. 12, 1995.
"Walgreens, Arbor set new benchmarks: Industry's top chain notches 20th record year. Net Income Jumped 14.9% to 281.9 Mil in FY 1994", Drug Store News, p. 15, James Frederick, Oct. 24, 1994.
"Reform plans boost mail–order drug firms", Crain's Chicago Business (IL), p. T2, Joanne Cleaver, Nov. 29, 1993.

*Primary Examiner*—Krista Zele
*Assistant Examiner*—Scott L. Weaver
*Attorney, Agent, or Firm*—Duane, Morris & Heckscher LLP

[57] ABSTRACT

Interactive medication data systems and methods are provided which include an automated system for providing information pursuant to telephonic and electronic requests from callers. The system includes a database containing information for a variety of medications and functions to receive an incoming audio communication relating to a request for information concerning a specific medication. The audio communication contains an identifier which can be mapped to the medication. The software in the system matches the identifier with a portion of the information in the database relating to the medication, and then provides a signal which is representative of this information portion. The signal is then translated to an audio message, or written response for transmitting to the caller. The system of this invention is particularly valuable in providing medication information to patient's that have their prescriptions on an existing pharmacy management database system.

16 Claims, 1 Drawing Sheet

INTERACTIVE MEDICATION DATA TELEPHONY SYSTEM

This is a Continuation application of application Ser. No. 08/515,250, filed Aug. 15, 1995 now abandoned.

FIELD OF THE INVENTION

This invention relates to interactive medication databases which are capable of providing verbal and written information relating to specific medications and pharmaceuticals, and more particularly, to automatic interactive voice response systems which are capable of providing selective types of medication information related to or independent from prescriptions managed by pharmacy management systems.

BACKGROUND OF THE INVENTION

For many years, when patients required information about their prescriptions, it was necessary for them to ask a healthcare professional, such as a doctor, nurse or pharmacist. These professionals would either have the information readily available, or would refer to bound reference books for comprehensive drug information, such as the *Physician's Desk Reference*, or package inserts supplied by the manufacturer with the prescription drug or patient education monographs. The availability of important information related to side effects, dosage and possible adverse drug interactions was therefore limited by the hours kept by these healthcare providers.

Verbal information dispensed from physicians and pharmacists is often easy to forget, and patients often misplace, or find it difficult to understand written materials.

Efforts to automate the dispensing of medication information have included the use of 900 numbers for ordering printed drug information, or for conferencing with a live person for obtaining answers to specific inquiries. Medication information software has also been developed which can respond to the spelling of medication names with textual information.

Individual drug companies have additionally created telephony systems which receive requests for information for specific drugs. Such systems are generally limited to providing highly technical reports for practitioners about medications from a specific manufacturer.

While current efforts to automate the medication information process have had some limited success, there is a present need for a more comprehensive system for communicating important information relating to side effects, usage and general information for medications of every sort, independent of the specific manufacturer. There also remains a need for an interactive medication information system which provides immediate, on-demand answers to important questions of users at a level easily understood by the lay user and that is simple to use.

SUMMARY OF THE INVENTION

The first embodiment of the present invention provides a telephony method and system for providing automatic information relating to a variety of medications, whether these medications are prescribed or purchased over-the-counter. This specific system receives an incoming audio communication relating to a request for information concerning a specific drug. This communication includes an identifier that is easily accessible by the caller, such as the patient's prescription number, which can be mapped to the patient's medication, and then matched with a portion of the information in the database relating to that medication. This information portion can be represented by a digitized voice recording for side effects for that drug, for example. The system provides a signal which is representative of the information portion selected by the matching step, and then an audio message is delivered to the caller which is responsive to the incoming audio communication.

The present invention is equipped to provide automated verbal drug information by phone to callers who call about specific medications. The system is not limited to healthcare workers' office hours, and is ready whenever a patient requires information, even on an emergency basis. The present system can communicate with an external management system database to map the identifier assigned by the external management system to the patient's medication, and to document what information has been delivered to the caller. The present system can be provided with data relating to general information, usage, side effects, drug interactions, and general precautions for the most widely prescribed drugs. It can be equipped to offer callers the option of obtaining hard copies of this information, for example, by mail or facsimile.

The present invention reduces staffing costs which were previously necessary in responding to patient inquiries, enhances patient services, and automatically tracks requests for specific medical information which may be required for complying with standards set by accreditation agencies. This invention accurately identifies specific medications by means of a novel identifier, such as a prescription number that can be mapped to a medication signature in a pharmacy management system that generated the prescription number, and thereafter, matched to the medication information database to automatically provide instant verbal or written medication information, or both, to callers over the phone by mapping, and reporting from, a pharmacy system database accessible through a MUMPS system.

A BRIEF DESCRIPTION OF THE DRAWINGS

The accompanying drawings illustrate preferred embodiments of the invention according to the practical application of the principles thereof, and in which:

FIG. 1 is a diagrammatic flow diagram of a preferred interactive medication information telephony system of this invention.

GLOSSARY OF TERMS

"audio communication"—a signal representing an audible sound, which can be regenerated into a sound if needed.

"telephony"—relating to computer-controlled processing of audio communications over a telephone network.

"mapping" or "mapped"—a process whereby existing associations between identifiers and targets are used to always resolve to the same target for a given identifier.

"usage"—background information relating to a given medication which may include general topics, such as why the medication is prescribed, how to store and administer the medication, what to do if a scheduled dose is skipped, etc.

"host system"—when the IVR functions are considered peripheral to functions performed on a separate system unit, and the IVR system relies on the separate system unit for data necessary for the IVR functions, then the separate system is called a "host system."

"pharmacy management system"—an automation technology used to manage processes relevant to the dispensation of medications to patients based on prescriptions generated by healthcare providers.

"telephonic audio inquiry"—an audio communication received over a telephone network that maps to a specific inquiry intended by the originator of said audio communication, such that said inquiry can be processed, directly or indirectly, by the IVR system, with the intention of eventually responding to said inquiry by the IVR system in a manner intelligible to or specified by the originator.

A DETAILED DESCRIPTION OF THE INVENTION

Interactive medication data telephony systems and methods are provided by this invention. A preferred version of this invention can operate with the popular MUMPS database used by many pharmacy management systems. The preferred embodiment enables callers to use interactive voice response technology to obtain verbal medical information by having the system map their prescription numbers to a corresponding medication.

MUMPS is a programming language, data management system and operating environment. There are formal ANSI, FIPS and ISO standards for MUMPS, as well as national standards from other countries. The ANSI standard includes a suite of specifications for internetworking and bindings to other technologies. MUMPS became the 3rd ANSI standard language, after COBOL and FORTRAN, and until the PROLOG standard is approved, MUMPS remains the only ANSI standard that encompasses a programming language with persistent data elements (i.e., a database). While MUMPS is used extensively in the healthcare area in the U.S. (as well as banking, collections, freight-forwarding and other areas), there is nothing about MUMPS that is inherently "medical." In fact, overseas it is used more in business. The Programming Language Special Interest Group of the American Computing Machinery Association listed MUMPS as one of the 5 or 6 true general purpose programming languages out of the several hundred they evaluated some years ago.

This invention relies upon interactive voice response technology (IVR), which enables callers with ordinary telephones to query or update computer systems. This effectively turns plain telephones into interactive terminals. Voice Mail and Bank-by-phone are the classic IVR applications used regularly by most people. IVR technology also allows computer systems to proactively "reach out and touch someone" to deliver information. For example, calling patients during the evening to remind them of upcoming appointments has been shown to reduce no-show rates effectively.

Two additional software features are utilized by the preferred embodiments of this invention for coordinating the medication database and IVR system with requests by callers for specific information. The first is an identifier which is easily accessible to, and easily inputted by the caller. This identifier enables the system to determine what medication the caller is interested in. The second is software which maps the identifier to a subset of information for a specific medication in a larger medication database. This not only provides specific information requested by the patient, but also can provide a fingerprint of the request itself, enabling a medical care provider or pharmacy to track inquiries into the system.

With reference to FIG. 1, the individual features of the preferred system will now be discussed. The database of this invention is initially accessed when the patient, healthcare worker, or significant other, calls the system 10. This group may include family members who may not have been present when the medication was first prescribed and any initial consultation was provided. The system welcomes the caller and provides generic usage information 20 for operating the system.

Following a short introduction, the system prompts the patient for a medication identifier 30 or access code, or both. The medication identifier should be unique to the patient's medication so that the system can track the portion of its database which is responsive to the caller's inquiry. This identifier can be a prescription number, which has been previously identified with a particular medication, or any arbitrary alpha-numeric code or code name, other than the letters that spell the name of the drug, which triggers the system to look for specific database portions.

Additional identifiers can include, for example, the digital image of the caller's voice pronouncing the name of the medication. Such images can be used to identify the medication independently from the caller's voice pattern.

Once the patient provides the medication identifier 40, the system software, entitled "Rx/INFO" maps the medication identifier 50 to the portion(s) of the database which have been previously programmed with textural, analog, digital or recorded information particular to that medication. If the software cannot validate the access code or the identifier against a database, such as a host system patient record database, a message is delivered, or played, which reports this event to the caller. A second, or third, etc., request for identification information can thereafter be made.

At this stage, the system searches the database to see if medication information is available for this particular prescription 70. In order to accomplish this, the system maps the prescription number to a medication signature in the host system pharmacy database. This can be accomplished by mapping the medication signature to a universal index supported by the system's software, then it can follow the index to check if the appropriate medication information is available for that medication. Assuming this information is found, the caller is then provided with a relevant set of offerings. These offerings can include, for example, general information about the specific medication, usage, side effects, precautions to follow while using the medication, and site-specific information. The caller selects the desired type of information from the option list 80, medication information selected by the caller is then provided 90. If any of the information has been modified or added by the local database site, the software can generate a verbal communication which tells the caller that the particular information provided is site-specific, as opposed to information which is offered as part of the standard medication information.

Finally, the Rx/INFO software documents in the host system patient record that an inquiry has been made using the particular identifier or code 100.

The patient is then offered the option of specifying another medication, using a separate identifier, such as a code, or prescription number 110. If the patient accepts, the cycle is repeated back 120 to the prompting step 30. Upon finishing with the inquiries, the patient is done with the system and hangs up 130. Of course, the patient may hang up at any time during the call and the system can also be equipped to record this event.

It is understood that this invention can operate using existing IVR hardware and software, database access technologies including a system server, voice database, voice synthesizer or audio recordings, and personal computers. Initially, the system is designed to accept several hundred different medications which represent the majority of the prescriptions handled by most pharmacies.

In the preferred system, the callers or patients must have their medication profile on a pharmacy management system or similar database to which this invention is interfaced. The system is especially designed to communicate with existing pharmacy management system databases to document the date and time when information was delivered to someone having access to a patient's identification code or prescription number. Verbal responses, as well as a subsequent release of a hard copy of this information can be printed, mailed, released to a terminal or sent by facsimile.

In one preferred embodiment of this invention, the pharmacy management system database is represented by a MUMPS host system, which can be located in a main frame or local area network. The Rx/INFO software operates in conjunction with a MUMPS TALK™ IVR server and accesses the host system through a suitable ETHERNET network. Callers, operating ordinary telephones, call into the voice server which identifies the caller with an access code, a prescription number, or both. The operating software, acting in conjunction with the voice server through the ETHERNET network, selectively accesses portions of the host system, pulls specific information relating to the caller's medication through the ETHERNET network and generates an oral communication through a phone line back to the caller. Such hardware can be equipped with standard analog phone lines as needed. The MUMPS TALK™ server can be configured as a LAT host. This enables it to print reports to any terminal on the network, or allow authorized users to log onto the system from their existing terminals.

From the foregoing, it can be realized that this invention provides improved interactive systems for providing callers with specific medication information 24 hours a day, 7 days a week. The system responds with spoken or written medication information about drugs including general information, dosage, side effects and precautions to follow while taking the medication. Medical centers and pharmacies may choose to have the present system help patients with initial consultations, as well as subsequent follow-up inquiries. Patients may listen to the recorded consultations at the medical center, and if unanswered patient questions remain, the questions can be answered by pharmacy personnel. The consultations provided by this invention meet OBRA and JCAHO requirements and work well with prescription refill software applications. The system can be customized to provide other options and voice messages can be delivered for special needs. The system also has the capability of transferring the caller to an attendant if the situation merits.

Although the various embodiments have been illustrated, this is for the purpose of describing, but not limiting this invention. Various modifications, which will become apparent to one skilled in the art, are within the scope of this invention described in the attached claims.

What is claimed is:

1. An automated telephony method comprising:
   (a) providing an informational database containing information for a variety of medications and a host system database containing signatures for at least some of said variety of medications;
   (b) receiving an incoming audio communication relating to a request for information concerning a specific medication; said audio communication containing a unique identifier which contains a prescription number which has been previously dispensed with said specific medication, said identifier being mapped to a signature for said specific medication in said host system database;
   (c) matching said signature with a portion of the information in said informational database relating to said specific medication;
   (d) providing a signal which is representative of said portion of information relating to said specific medication; and
   (e) transmitting a message concerning said specific medication generated from said signal which is responsive to said incoming audio communication.

2. The telephony method of claim 1 wherein said informational database comprises a plurality of types of information.

3. The telephony method of claim 2 wherein said types of information comprise usage, side effects, precautions, and general background information for said specific medication.

4. The telephony method of claim 1 wherein said host system database comprises a pharmacy database.

5. The telephony method of claim 4 further comprising recording onto a patient record an indication that a medication consultation has been delivered to a caller.

6. An automated telephony method comprising:
   (a) providing a medication information database containing usage and precautionary information for a variety of medications and a host system database containing signatures for at least some of said variety of medications;
   (b) receiving an incoming telephonic communication relating to a request for specific information for a specific medication; said telephonic communication containing a unique identifier which contains a prescription number which has been previously dispensed with said specific medication, said identifier being mapped to a signature for said specific medication contained within said host system database;
   (c) matching said signature to said specific information; and
   (d) providing an outgoing message relating to said specific information which is responsive to said incoming telephonic communication.

7. The telephony method of claim 6 wherein said identifier comprises a code affixed to a medication container.

8. An automated interactive telephony system comprising:
   (a) an informational database containing information for a variety of medications and a host system database containing signatures for at least some of said variety of medications;
   (b) a receiver for receiving an incoming audio communication relating to a request for specific information relating to a specific medication, said audio communication containing an identifier which is unique to a unique prescription for said specific medication and which can be mapped to a signature for said specific medication in said host system database;
   (c) processing means for receiving said audio communication from said receiver, for matching said signature with a portion of the information in said informational database relating to said specific medication, and for providing a signal which is representative of said information portion; and
   (d) transmitter means for receiving said signal from said processing means and for sending a message relating to said specific medication which is responsive to said incoming audio communication.

9. The telephony system of claim 8 wherein said receiver and transmitter means comprise a telephone voice processing card.

10. The telephony system of claim 8 wherein said identifier comprises a code specifiable over a phone system by a caller.

11. The telephony system of claim 8 wherein said host system database comprises a pharmacy database.

12. The telephony system of claim 8 wherein said processing means comprises a computer.

13. The telephony system of claim 8 wherein said processing means comprises mapping software that maps said identifier to the specific medication in a pharmacy database.

14. The telephony system of claim 8 further comprising means for documenting whether a message has been sent.

15. An automated interactive telephony system comprising:

(a) a telephone voice processing receiving means for receiving an incoming telephonic audio inquiry relating to a request for specific drug information, said audio inquiry containing an identifier which is unique to a unique prescription for said specific medication and which can be mapped to a signature for said specific medication in a host system database;

(b) a medication information database containing information for a variety of medications;

(c) computer processing means for receiving said audio inquiry from said telephone voice processing receiving means, for matching said signature to a portion of the information in said medication information database relating to said specific medication, and for transmitting a signal which is representative of said information portion; and (d) telephone voice processing transmitter means for receiving said signal from said computer processing means and for sending an audio message relating to said specific medication which is responsive to said incoming audio inquiry.

16. An automated method of providing information relating to a medication in response to an incoming electronic communication, comprising:

providing an informational database containing information for a variety of medications and a host system database containing signatures for at least some of said variety of medications;

receiving an incoming electronic communication from a sender relating to a request for specific information concerning a specific medication; said electronic communication containing a code which is unique to a unique prescription for said specific medication and which can be mapped to a signature for said specific medication on said host system database;

matching said signature to said specific information in said informational database; and providing a message to said sender which is derived from said specific information and which is responsive to said incoming electronic communication.

* * * * *